United States Patent [19]

Capel

[11] Patent Number: 4,646,744

[45] Date of Patent: Mar. 3, 1987

[54] METHOD AND TREATMENT WITH TRANSCRANIALLY APPLIED ELECTRICAL SIGNALS

[75] Inventor: Ifor D. Capel, Chaldon, England

[73] Assignee: Zion Foundation, London, England

[21] Appl. No.: 626,335

[22] Filed: Jun. 29, 1984

[51] Int. Cl.$^4$ ............................................. A61N 1/36
[52] U.S. Cl. ............................................. 128/423 R
[58] Field of Search ................ 128/419 R, 421, 422, 128/423 R

[56] References Cited

U.S. PATENT DOCUMENTS

| | | | |
|---|---|---|---|
| 2,771,554 | 11/1956 | Gratzl | 128/421 |
| 3,025,858 | 3/1962 | Browner | 128/422 |
| 3,946,745 | 3/1976 | Hsiang-Lai et al. | 128/421 |
| 3,983,881 | 10/1976 | Wickham | 128/421 |
| 4,294,245 | 10/1981 | Bussey | 128/421 |
| 4,305,402 | 12/1981 | Katims | 128/421 |
| 4,315,503 | 2/1982 | Ryaby | 128/421 |

Primary Examiner—William E. Kamm
Attorney, Agent, or Firm—Vaden, Eickenroht, Thompson & Boulware

[57] ABSTRACT

A method of applying an electrical signal transcranially includes the steps of generating a series of signal trains and applying the signal trains across the head of a subject, wherein each of the trains comprises a number of pulses and is separated from other trains by off periods, during which the signal is not applied. The signal trains are of such short duration that substantially no nerves within the subject's brain that receive the signal trains are demyelinized. In certain embodiments, the signal trains and the off periods are of irregular duration such that the activation of nerves of the brain by a signal is of a substantially continuous rate as the application of the signal train proceeds. The invention also includes particular characteristics of signals used to treat respective afflictions, including drug addictions and habituations, appetite disturbances, stress, insomnia, and pain.

40 Claims, 5 Drawing Figures

METHOD AND TREATMENT WITH TRANSCRANIALLY APPLIED ELECTRICAL SIGNALS

BACKGROUND OF THE INVENTION

I. Field of the Invention

This invention pertains to a method of transcranially applying electrical signals in order to treat afflictions including drug addictions and habituations, appetite disturbances, stress, insomnia, and pain.

II. Background of the Invention

The individual and societal tragedy of drug and alcohol abuse is well known and statistics demonstrate that prior art treatment methods for addictions and habituations have been unable to control the problem. With regard to applications of electrical signals to cope with these and other afflictions, such inadequate treatment methods include conventional transcutaneous electrical nerve stimulation therapy (TENS), electro-acupuncture, and invasive electrical treatments.

Conventional TENS treatment is based on the Melzack and Wall gate theory of pain, which basically suggests that pain can be ameliorated or masked by providing an electrical signal to a body segment in order to counteract a pain signal that is being transmitted to the brain from the body segment along small α-afferent nerve fibers. According to this theory, the "gate" located in the substantia gelatinosa region of the brain, through which the pain signals normally pass, is effectively closed by applying the counteractive TENS signal. As will be seen, conventional TENS treatment is thus based on a different theory of action that provides only the amelioration or masking of pain and, as a result, involves the use of signals and modes of applying the signals which are clearly distinguishable from the transcranial methods described hereinbelow.

Electro-acupuncture is similarly distinguishable from the present invention. As is well known, acupuncture involves the placement of needles at appropriate points, known as acupoints, and it is believed by some that the application of electrical currents to the needles can enhance the production of certain neurotransmitters in the brain. There is no evidence that the prior art electro-acupuncture techniques can serve to affect the mechanics of drug addiction at the neurosynaptic junctions where the drug interacts, nor that other of the enumerated afflictions can be successfully treated by electro-acupuncture.

Other prior art techniques can be characterized as invasive techniques in that they actually involve the insertion of the electrodes into regions of the brain, in particular, the peri-aqueductal grey region, wherein electrical signals generated by the electrodes are said to cause stimulations to modify the production of certain neurotransmitters. As these techniques actually require a form of brain surgery, they are limited in application, such as to those cases where the patient's life is threatened or where the patient has a terminal affliction.

Accordingly, it is an object of the present invention to provide an effective method of treatment with transcranially applied electrical signals for the afflictions of drug addiction and habituation, appetite disturbances, stress, insomnia, and pain without the need for the insertion of probes or electrodes into the patient's body.

It is a further object of the present invention to provide a method that acts by introducing an electrical signal across the head to treat the affliction at the neurosynaptic junctions where the affliction often originates.

It is a further object of the invention to provide a method that acts by introducing an electrical signal across the head to modify the production of neurotransmitters.

It is a further object of the invention to provide a method of treatment with transcranially applied electrical signals wherein substantially no nerves within the brain become demyelinized.

It is a further object of the invention to provide a method of treatment with transcranially applied electrical signals wherein the targeted nerves do not become acclimatized to the electrical signal.

It is a further object to provide an electrical signal across the head having characteristics that are effective to alleviate or eliminate at least one of the above-enumerated afflications or other afflictions that often originate at the neurosynaptic junctions of the brain.

It is a further object to provide a method of treatment with transcranially applied electrical signals, wherein the applied signal can be altered in an emergency situation to relieve any discomfort encountered by the patient.

It is a further object to provide a method of treating drug addiction with transcranially applied electrical signals to ameliorate or eliminate all withdrawal symptoms that otherwise may be experienced during a controlled detoxification and rehabilitation program.

It is a further object of the invention to provide a method of treatment with transcranially applied electrical signals whereby the monitoring of the progress and efficacy of the treatment can be continuous.

It is a still further object of the invention to provide a method of treatment with transcranially applied electrical signals wherein the patient is unable to distinguish when a signal is being applied and when it is not.

These objectives are satisfied in the practice of the present invention.

SUMMARY OF THE INVENTION

In accordance with the invention, a method of applying an electrical signal transcranially includes the steps of generating a series of signal trains and applying the signal trains across the head of a subject, wherein each of the trains comprises a number of pulses and is separated from other trains by off periods, during which the signal is not applied. The signal trains are of such short duration that substantially no nerves within the subject's brain that receive the signal trains are demyelinized. In certain embodiments, the signal trains and the off periods are of irregular duration such that the activation of nerves of the brain by the signal is of a substantially continuous rate as the application of the signal trains proceeds. The invention also includes particular characteristics of signals used to treat respective afflictions, including drug addictions and habituations, appetite disturbances, stress, insomnia, and pain.

DESCRIPTION OF THE PREFERRED EMBODIMENTS

The present method of treatment involves the transcranial application of electrical signals of definite character and duration to treat a variety of afflictions, including drug addictions and habituations, appetite disturbances such as obesity and anorexia nervosa, stress, insomnia, and pain. A person diagnosed as being afflicted with one of these conditions is prescribed a treatment regimen in accordance with the present invention. The regimen is specific to the affliction and generally involves a one or two stage application of electrical signals across the patient's head. Preferred treatment regimens for particular afflictions are set forth below. It will be appreciated that the following teachings can be appropriately modified without departing from the spirit of the invention.

In accordance with the present invention, treatment of drugs that are received by opiate receptors are treated by the application of two signals having frequencies of 100 Hz and 10 Hz, respectively. The 100 Hz frequency is applied in a first stage of treatment that lasts for 5 to 7 days. The signal is applied during the first stage in a direct current and preferably has a pulse width of 0.22 msec., but the pulse width is increased to 0.5 msec. if the shorter pulse width cannot be tolerated by the patient. Importantly, the 100 Hz frequency is applied intermittently in trains of pulses, spaced apart by off periods during which no signal is applied. The duration of the trains is dependent upon the frequency of consumption of the drug of abuse. If the drug was taken in more than two doses during the addict's waking hours, continuous application of the intermittent treatment is preferred, ideally in trains of 100 seconds, each separated from another by off periods of 100 seconds. After 5 to 7 days of treatment with the high frequency signal, a signal having a frequency of 10 Hz is applied in an alternating current in a second stage of treatment. The pulse width of the low frequency signal is 1.5 msec. The low frequency signal is applied intermittently in pulse trains, similar to the application of the high frequency signal during the first stage, but also irregularly, such that the average ratio of the duration of on periods to off periods is initially constant, but the duration of individual on and off periods is irregular, as more fully discussed hereinbelow. After 2 to 3 days of treatment under the second stage, the average duration of the off periods is gradually increased, and this process constitutes a weaning off period.

Drugs that are received by opiate receptors, addictions to which are treated in accordance with the above, include opium, morphine, heroin (diamorphine, diacetyl morphine), dihydromorphinone (hydromorphone), metopon (methyl dihydromorphinone), levorphanol, codeine (methyl morphine), oxymorphone (dihydrohydroxy morphinone), hydrocodone (dihydrocodeinone), oxycodone (dihydro-hydroxy codeinone) meperidine (pethidine), phalcodine (β-morpholinyl ethyl morphine), methadone, phenazocine, etorphine, dihydrocodeine, dextromoramide, dipipanone, phenadoxone, alphaprodine, amleridine, piminodine and apomorphine.

With regard to barbiturates and barbiturate-like sedatives, two signals having different frequencies are applied in an alternating current, one for use during the patient's waking hours and one for use during a sleep period. The signal applied during waking hours has a frequency of 25 to 35 Hz and a pulse width of 0.1 msec. The signal applied during waking hours is presented in trains of pulses of irregular duration, the average duration of the trains being dependent upon the frequency at which the addict consumed the drug of abuse. If more than two doses were taken by the patient during waking hours, then a continuous application of trains of irregular duration is administered for five days, preferably with trains having an average duration of 30 seconds, each of said trains being separated by off periods of an average duration of 30 seconds. After one day of treatment, a constant application of a signal having a 10 Hz frequency is applied during the sleep period. This lower frequency signal has a pulse width of 1.5 msec. After 5 days of treatment, a weaning off process is initiated in which the off periods between the application of the trains of pulses having 25 to 35 Hz frequencies are increased in duration. The weaning off process is continued for 5 days. At any time at which an emergency arises, in which the patient has an adverse reaction such as convulsions, the signal is immediately changed to one having a 500 Hz frequency and 0.2 msec. pulse width in a direct current. The non-emergency treatment schedule resumes one hour after the emergency situation abates.

Barbiturates and barbiturate-like sedatives, habituations to which are treated in accordance with the above, include amylobarbitone (amobarbitone), allobarbitone, aprobarbital, barbital (barbitone), butabarbitone (butabarbital), phenobarbitone (phenobarbital), cyclobarbitone, pentobarbitone (pentobarbital), quinalbarbitone (secobarbital, thiamylal), hexobarbitone (hexobarbital), methohexitone (methohexital), thiopentone sodium (thiopental), thialbarbitone, mephobarbital, metharbital, probarbital, talbarbital, Nembutol, seconal and tuinal.

In the case of habituations to Valium and other benzodiazeapines, a signal having a frequency of 200 Hz and a pulse width of 0.5 msec. is applied intermittently in a direct current. Trains having durations of 200 seconds are preferred, separated by off periods of 200 seconds. The treatment for this type of addiction lasts less than 14 days. In the event that the patient becomes unduly stressed, the treatment is discontinued and substituted with a treatment for 5 days with a signal having a 10 Hz frequency and 1.5 msec. pulse width, applied in an alternating current in intermittent and irregular trains having an average duration of 10 seconds. After the 5 day emergency treatment period is completed, the treatment reverts to an additional 5 days of the regular treatment. In accordance with the above, treatment is administered for habituations to other benzodiazepines such as chlordiazepoxide hydrochloride, chlordiazepoxide, chlorazepate dipotassium, diazepam, and oxazepam.

For cocaine addiction, a signal having a frequency of 30 Hz and a pulse width of 0.1 msec. is applied in an alternating current. The signal is applied in trains of irregular duration and, preferably, in trains having an average duration of 30 seconds, each separated by off periods each having an average duration of 30 seconds. The treatment lasts for less than 7 days and during that period, if the patient becomes restless, the signal is changed to one having a frequency of 200 Hz and a pulse width of 0.5 msec., applied constantly in a direct current. This emergency application continues for one hour after such restlessness ceases, followed by a 24 hour period during which the 200 Hz signal is applied in trains of 200 seconds duration, separated by 200 second off periods.

With regard to amphetamines, including amphetamine, dexamphetamine (dextroamphetamine), amphetamine sulphate (Benzedrine), dextroamphetamine sulphate (Dexedrine), and methamphetamine (ephedrine sulphate), a signal having a frequency of 200 Hz is applied in a direct current. During the patient's waking hours, the signal has a pulse width of 0.5 msec. and is applied in intermittent trains. Preferably, the duration of the trains and the off periods between the trains is 200 seconds. During a sleep period, the pulse width is changed to 1.5 msec. and the signal is applied continuously. The treatment for amphetamines lasts for less than 7 days.

In order to treat a patient habituated to nicotine, a signal having a frequency of 5 to 10 Hz and a pulse width of 0.1 or 0.22 msec. is applied in an alternating current for 7 successive treatment days. Ideally, the signal is applied in intermittent trains of irregular duration, preferably in trains each averaging 5 seconds in duration and separated by off periods each averaging 5 seconds. The average duration of the on and off periods is increased in a progression to a predetermined maximum duration of about 30 minutes, at which point the average duration is then progressively reduced until the original average duration of 5 seconds on and 5 seconds off is achieved.

Alcohol addictions are treated with a signal having a frequency of 10 Hz and a pulse width of 0.1 msec. in an alternating current during the waking hours. The signal is applied in pulse trains of irregular duration, preferably averaging 10 seconds, separated by off periods of 10 seconds average duration. During a sleep period, a signal having a frequency of 30 Hz and a pulse width of 1.5 msec. is constantly applied. The length of the treatment will vary depending upon the level of addiction, but does not exceed 14 days. If an emergency situation arises in which the patient manifests discomfort, a signal having a frequency of 200 Hz and 0.5 msec. pulse width is applied in a direct current for one hour. After the crisis passes, the regular treatment is resumed. In the event of a second emergency situation, the high frequency signal is again introduced and maintained for up to 5 days, followed by the regular treatment for an additional 5 days.

When treating addictions to hallucinogenic drugs, including cannabis (hashish, marijuana), cannabinol, cannabidiol, cannabinolic acid, cannabigerol, cannabicyclol, tetrahydrocannabinol, lysergic acid diethylamide (LSD), psilocybin, psilocin, and mescalin, a signal having a frequency of 200 Hz and a pulse width of 0.5 msec. is applied in a direct current. The signal is applied in intermittent pulse trains, preferably of 200 seconds duration, separated by off periods of 200 seconds during the patient's waking hours. If the patient's condition is complicated by insomnia, a signal having a frequency of 10 Hz is applied as in the case of treatment for barbiturate habituation, discussed hereinabove. The treatment for hallucinogens lasts less than 7 days. If depression results during the treatment, a signal having a frequency of 10 Hz and a pulse width of 0.22 msec. is applied in short trains for one hour. Ideally, the use of the low frequency signal is avoided.

Pain is alleviated by intermittently applying a signal having a frequency of either 10 Hz or 200 Hz. If a 10 Hz frequency is applied, it has a pulse width of 0.22 msec. during the day and 1.5 msec. during the night, and will preferably be applied in signal trains of irregular duration in an alternating current. If the 200 Hz frequency is employed, it will have a pulse width of 1.5 msec. in a direct current. Stimulation with the low frequency signal is appropriate for all painful conditions. Stimulation with the high frequency signal is appropriate for some patients having low back pain or terminal cancer.

An important aspect of the treatments outlined above is that the application of the signal is not continuous but is instead intermittent. The use of the intermittent current is important both when signals of relatively high (about 100 Hz or more) and relatively low frequencies (about 35 Hz or less) are being applied. With regard to the low frequency signals, it is also important that the duration of signal trains and the intervening off periods also be irregular. In the case of a low frequency signal, continuous application causes the nerve to be acclimatized to the signal, whereupon the nerve tends to ignore it. Consequently, if the low frequency signal is intended to cause the nerve to stimulate the production of neurotransmitters, the amount of neurotransmitter produced will be reduced. It is possible to apply intermittent on and off periods, wherein the periods are of regular duration, but it has been found that the targeted nerves have the capability of recognizing the regularity of unvarying on and off periods and, as a result, the acclimatizing of the nerves remains a problem. In accordance with the present invention, the solution has been found in the application of on and off periods of irregular duration, whereby the targeted nerves cannot recognize the regularity of the applied signal. Instead, the nerves act as if new signals are continually being applied, so that the activation of the nerve by said signal is not significantly reduced as the application of the irregular treatment proceeds, resulting in a substantially continuous rate of neurotransmitter production during stimulation.

The important characteristic of the irregularity of the durations of the on and off periods is that it be sufficiently irregular so that the targeted nerves cannot discern the pattern of application. Preferably, the irregularity will be such that no two successive periods of stimulation have the same duration and no two successive off periods have the same duration, but such complete irregularity is not required. The occurrence of successive on periods or successive off periods having durations of equal length would be tolerable at least to the extent that such successively equal periods would be generated in a randomly selected series of durations. In a preferred embodiment, the duration of the pulse trains is determined by a logarithmic or arithmetic progression so that a determination of the nature of the treatment being applied to a patient can be more readily obtained at any given moment. It has been found that the nerves do not become acclimatized to signals applied in such progressions, and the ability to readily determine whether a signal is being applied can be beneficial for therapeutic and research purposes.

With regard to signals of high frequency, it is important that the signal be applied intermittently. When the signal having a high frequency is applied to block a nerve impulse, there is a likelihood of ion migration from the nerve and in addition, there is a possibility that there might be a degree of nerve demyelinization. By presenting the signal intermittently, the nerve has time to recover and reorient itself in terms of its ionic composition, so that excessive ion migration and nerve demyelinization do not occur.

In the treatment of drug addictions, consideration should be given to the regularity at which a drug of abuse was illicitly taken prior to treatment, in order to determine the length of time that the on and off periods of stimulation are applied. The patient who consumed the illicit drug more often is administered the electrical signal with only short off periods interjected between whole trains. Thus, for an addict who regularly abused a drug such as cocaine at 10 minute intervals, the electrical stimulation is not off for more than one minute at a time. On the other hand, if the patient is an addict who abused a drug in cycles of 6 hours or more during waking hours, the stimulation pattern need not be restricted to a pattern having a very short off period. Thus, in this latter case, the signal and off period could each first be applied for one minute, then 10 minutes, then 100 minutes, then 1000 minutes, and then revert back to 100 minutes, then 10 minutes, and then one minute. It is noted that, for the treatment of certain types of afflictions, such as the pain experienced by cancer patients, it has been found that the most effective treatment has been achieved by shortening the periods during which the signal is on and shortening the off periods.

As noted above, it is an object of the present invention to treat the afflictions of addictions and habituations to drugs, including alcohol and nicotine, appetite disturbances, stress, insomnia and pain by modifying the production of neurotransmitters in the brain. As a model to demonstrate the effect of the present invention on such neurotransmitter production, the following describes the effect of the present treatment in the case of heroin addiction. While this theory of action is set forth to more fully describe the operation of the present invention, the operational teachings included herein are not intended in any way to be dependent upon the theoretical teachings, and the scope of the appended claims are not diminished in any way by virtue of the following theoretical presentation.

When a person receives a dose of heroin, heroin molecules compete with naturally produced substances of the body, known as neurotransmitters, at receptor sites at post-synaptic nerve junctions. One particular type of neurotransmitter, or endorphin, with which the heroin competes is leuenkephalin. Studies have shown that leuenkephalin, when naturally produced and received at its corresponding receptor sites at post-synaptic nerve junctions, produces a pleasant or euphoric feeling but, when leuenkephalin is not received at its receptor sites but instead remains free, unpleasant conditions, including convulsions, can occur. After repeated doses of heroin, the receptor sites naturally reserved for leuenkephalin are substantially continually blocked by the heroin molecules and the brain, in an attempt to compensate for the presence of the artificial substance, reduces or shuts down the natural production of leuenkephalin. The result is a vicious cycle, wherein repeated doses of heroin are necessary to in turn compensate for the shutdown or reduction of leuenkephalin production.

In a normally functioning human being, only enough leuenkephalin is produced to effect the naturally intended result at the receptor sites, and after the intended result is effected, the neurotransmitter is inactivated. This occurs by the release of a particular enzyme to react with the neurotransmitter after it has been received at the post-synaptic dendrite and caused a depolarization of the post-synaptic nerve. The enzyme acts to remove the neurotransmitter from the receptor site in order that the neurotransmitter can either be metabolized and excreted or partially reabsorbed by the pre-synaptic vesicles and reserved for later use. When the receptor sites are instead occupied by heroin in the case of a drug addict, the post-synaptic depolarization and concomitant production of enzyme does not occur, so that any leuenkephalin produced remains in the body for long periods of time.

By applying an electrical signal having a relatively high frequency during a first stage of treatment and following this with the application of a signal having a relatively low frequency in a second treatment stage, the heroin addiction is treated by addressing the role of the drug at the neurosynaptic junction. During the first stage of treatment, the high frequency signal is received by the nerves that produce neurotransmitters such as leuenkephalin, and the signal is of such a nature as to inhibit the production of leuenkephalin by the corresponding leuenkephalin-secreting neuron termini. The signal is of such a high frequency that the nerve cannot recover from the initial stimulation, resulting in the nerve's failure to achieve depolarization and generate successive impulses. The nerve, in effect, becomes numb and the production of neurotransmitter is correspondingly inhibited. During this period, the heroin is removed from the receptor sites through natural metabolic processes and the production of leuenkephalin that might otherwise enter the body's system during the occupation of the receptor sites by the heroin molecules is inhibited. The duration of the first stage of treatment is dependent upon the length of time required to effect the removal of the heroin molecules from the receptor sites, which in turn depends upon the length of time of the addiction and the rate of drug consumption during the addiction.

Theoretically, the first stage of the treatment for heroin addiction is all that is necessary to detoxify the patient, but it has been found that, unless the second stage is applied, the patient experiences sometimes severe emotional distress and despondency. Accordingly, the second stage is applied, during which the signal having a frequency of 10 Hz acts conversely to the signal applied during the first stage, the result being that leuenkephalin production is enhanced during the second stage. It is believed that the enhanced production of leuenkephalin alleviates the deleterious symptoms that follow the first stage because, over the period of the drug addiction, the leuenkephalin secreting neuron termini have adjusted to the presence of the heroin by reducing the production of leuenkephalin. After the heroin is removed from the body at the end of the first stage of treatment, the leuenkephalin production is insufficient to occupy the vacated receptor sites, resulting in the emotional distress and despondency. By enhancing leuenkephalin production through the application of electrical stimulation, these conditions are alleviated.

In the treatment for heroin addiction, as with treatments for other addictions as outlined hereinabove, a weaning off period is initiated prior to the termination of the treatment. The weaning off consists of gradually increasing the duration of the off periods and, in the case of the treatment for heroin addiction, the purpose of the weaning off period is to allow the neurotransmitter-producing cells to gradually increase their production and to avoid any adverse effects caused by insufficient production of neurotransmitters, such as withdrawal symptoms. The weaning off period allows the body to resume its normal production without creating a dependency upon the electrical signal.

In the treatment schedules outlined above, it will be noted that many of the treatments do not require the application of a first signal during a first stage, followed by the application of a second signal during a second stage. This is because not all of the treatments require the initial elimination of the drug of abuse from the receptor sites, followed by a period of promoting the production of the body's neurotransmitters to replace the drug of abuse. Instead, in a number of the treatment methods outlined above, such as in the case of the barbiturate and barbiturate-like sedatives, it has been found that the application of a signal that stimulates the production of neurotransmitters is all that is necessary, whereby the stimulatory stage simply overcomes the overall inhibitory effect that the drugs have on the neurotransmitter-producing cells. Similarly, in the case of drugs such as amphetamines, only one stage of treatment is necessary, wherein a signal having a high frequency and acting to inhibit neurotransmitter production is applied. It is believed that amphetamine is metabolized to form a false transmitter that is taken up by excitory nerve endings and that the application of the signal having a high frequency operates to inhibit the metabolic process and allow for the rapid elimination of the false transmitter from the body.

Figure 1:
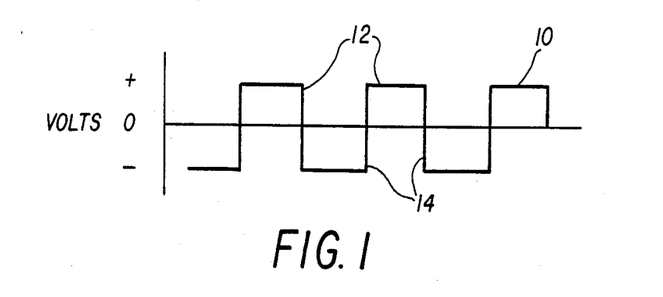
FIGS. 1 through 3 are schematic illustrations of three types of wave forms of signals applied in accordance with the invention.
Figure 2:
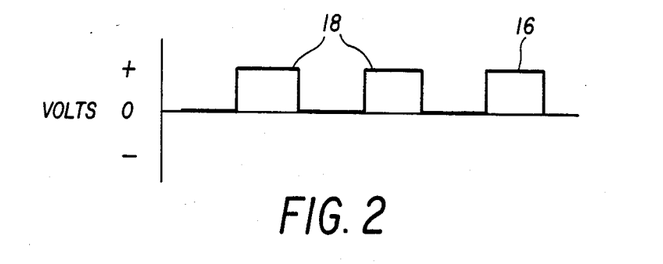

The signals applied in accordance with the present invention have a rectangular wave form or a modified rectangular wave form. A suitable wave form as would occur in the application of an alternating current is depicted in FIG. 1. A suitable wave form as applied in a direct current is depicted in FIG. 2. In FIG. 1, the wave 10 comprises positive segments 12 and negative segments 14. The positive and negative segments cancel each other out so that there is a zero net voltage. In FIG. 2, wave 16 is also of a rectangular form, but consists only of positive segments 18. It is noted that, with regard to certain transcutaneous electrical nerve stimulating devices, especially those employing a rapid recharge apparatus, a large spike sometimes 5 or even 10 times the intensity of the overall rectangular component of the signal precedes the rectangular component. In order to eliminate an undesirable spike, it is sometimes possible to allow the batteries to stand for 6 to 12 hours without any use.

Figure 3:
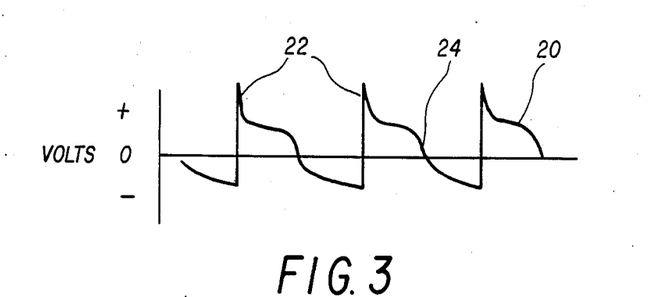

It has been found that the wave form generated naturally in the body to modulate the production of neurotransmitters is not necessarily of rectangular form. In FIG. 3, a wave 20 having a positive and a negative segment is depicted as it may occur in nature. The general shape of the rectangular wave of FIG. 1 is thus modified by the occurrence of a spike 22 at the onset of the pulse and a diminution of intensity 24 as the pulse progresses to termination of the positive segment. In a preferred embodiment, the signals applied in accordance with the invention have a wave form as depicted in FIG. 3.

Throughout the treatment schedules outlined above, the nature of the current is designated as being alternating or direct. It has been found that the application of an alternating current is superior because it is less likely to produce deleterious polarization effects than is a direct current. Accordingly, at least for the application of signals of relatively low frequency, i.e., about 35 Hz and below, the use of an alternating current is preferred. However, at higher frequencies, the beneficial effects of an alternating current are reduced and direct current is equally efficacious because, as outlined above, the present invention involves the application of the signals intermittently so that the possibility of deleterious polarization is reduced or eliminated. By applying the high frequency signal in an intermittent fashion, the nerves are periodically allowed time to rest and recover. The use of a direct current is preferred over an alternating current when a machine is used that generates pulses having unpredictable negative components, such as negative components with unpredictable shapes.

The pulse widths recited above in the outlines of the various treatments are preferred, but modifications of the pulse widths, in conjunction with modifications of the frequency, are made in accordance with the invention if the patient manifests adverse reactions to the treatment. Thus, in the treatment for drugs that react with opiate receptors, provision is made for the widening of the pulse width when the patient experiences a headache during application of the higher frequency stimulation, whereupon the headache can be alleviated or eliminated. The alteration of the pulse width in the emergency treatment phases, as outlined above, also has beneficial results. A pulse width of 1.5 msec. is used in the second stage of the treatment for addictions to drugs that react with opiate receptors and also during sleep periods for other of the treatments because it has been found that a wave of this pulse width tends to induce a general drowsiness and assists in the restoration of a normal sleep pattern. It is noted that pulse width as defined herein, is the width of an individual positive segment, as illustrated in FIGS. 1 to 3, of the wave.

In the practice of the invention, the signals preferably have a low voltage, one volt being sufficient. Although the application of a signal having a higher voltage can achieve beneficial results, the lower voltage is preferred since substantially the same effect can be achieved and practical advantages can be obtained. If a human subject receives a signal for a number of days, it is possible that charge can accumulate on the patient, and the accumulation is believed to be proportional to the amount of current that is being introduced. Accordingly, the application of the lower voltage results in greater safety for the patient. Another practical advantage of the application of a low voltage signal is the ability to apply the signal without the knowledge of the patient. The subliminal application allows the patient to be weaned off a particular signal without being psychologically distressed by its withdrawal and, further, allows for placebo studies to be practiced, whereby a patient does not know whether he is receiving a signal or a placebo treatment.

For similar reasons, it is preferred that the amperage of the signals applied in accordance with the invention be low. The amperage varies in accordance with the varying impedances of different individual patients and electrical contacts, but an amperage of less than 100 milliamps is sufficient.

The duration of the treatments outlined above varies in accordance with the patient's particular addiction. In the case of addiction to heroin, the first stage of treatment is said to last for 5 to 7 days, but it is noted that in certain cases, the first stage can be successfully completed within 2 to 3 days. The actual number of days required depends primarily upon the number of years of addiction and the quantity of drugs to which the patient has become habituated.

In the event that the patient experiences an adverse reaction during the treatments outlined hereinabove, action to alleviate the condition generally consists of the application of an emergency signal. When the adverse reaction takes place during the application of a low frequency signal, the emergency signal is typically characterized by a high frequency. Conversely, if the adverse reaction is experienced during the application of a high frequency signal, an emergency signal having a relatively low frequency can be applied to alleviate the condition.

Another important aspect of the present invention is the institution of a standardization step prior to treatment. Because the nature of many of the treatments varies as a function of time, it is important that patients be introduced to the treatments at a known point in the cycle of their drug usage. It has been found that the most effective way to establish the point is to administer a dose of the drug of abuse, or a clinically approved substitute that is functionally equivalent to the drug of abuse, to the patient under clinical supervision at the onset of the treatment. The application of the therapeutic signal is then applied after most of the effects of the drug have subsided but before the patient experiences withdrawal symptoms.

Figure 4:
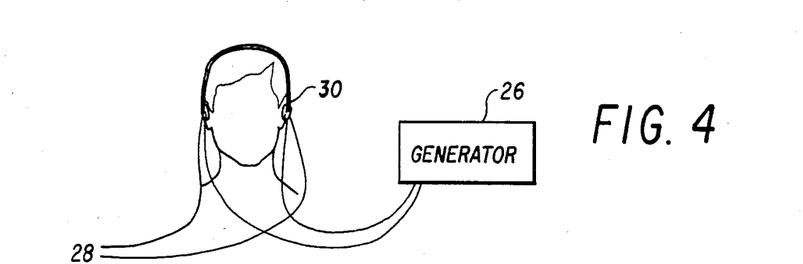
FIG. 4 is a schematic diagram of equipment that has been supplied to a subject for receiving a signal in accordance with the invention.
Figure 5:
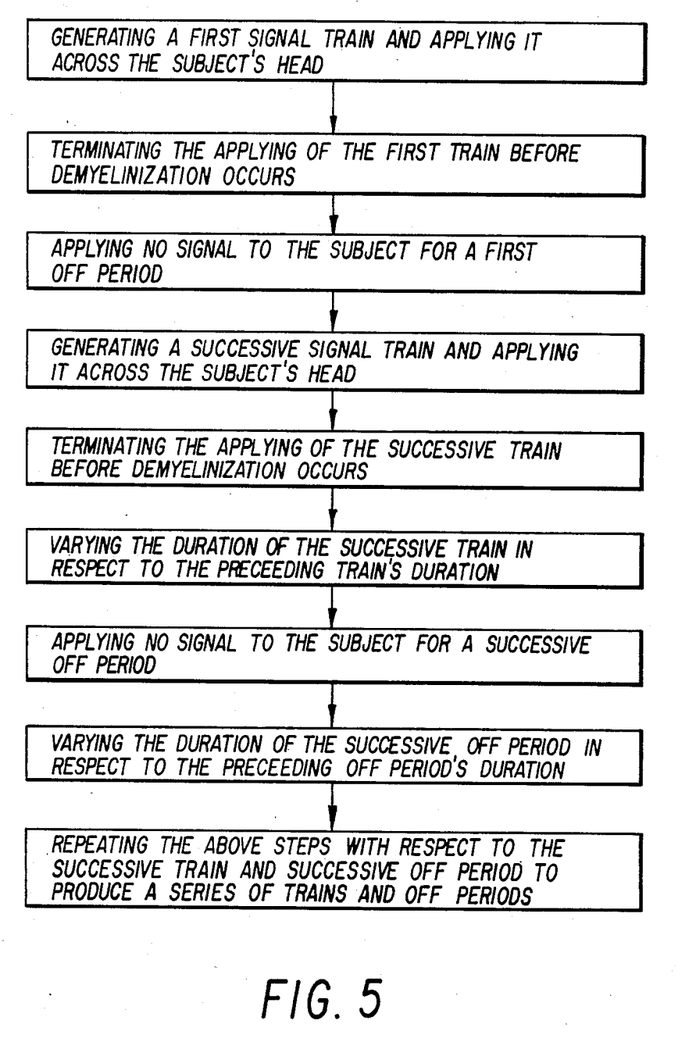
FIG. 5 is a flow diagram of the treatment steps of the method of the invention.

A machine suitable, with modifications, for the generation and application of signals in accordance with the present invention is manufactured by European Electronic Systems, Ltd. of England, and is known as the EES Mark II or the Pharmakon-Patterson NeuroElectric Stimulator Model IV. The above-stated characteristics of the signals applied in accordance with the invention have been determined by reference to the controls of this machine. In addition, any machine capable of generating signals having frequencies, pulse widths, voltage, current, and wave forms as described above is suitable in the practice of the invention. FIG. 4 includes a depiction of signal-generating machine 26. In order to generate trains and off periods of the desired duration, in accordance with the present invention, a simple manual switching means, well known to those skilled in the art, can be introduced into the circuitry of the apparatus.

In an especially preferred embodiment, an oscilloscope is used to constantly monitor the wave form and magnitude of the signal as it is received by the patient. The use of an oscilloscope is especially important, since the impedance of the skin can change during the course of the treatment. The oscilloscope also monitors the connection of the electrode to the skin, such that a faulty connection that occurs at some point during treatment will not go unnoticed.

As indicated above, the signal generating apparatus is provided with electrodes 28 to transmit the generated signal to the head 30 of the patient, as depicted in FIG. 4. The positive electrode is attached to the ear on the side of the head that corresponds to the dominant hand of the subject, i.e., the right ear is the point of attachment for a right-handed individual and the left ear is the point of attachment for a left-handed individual. A considerable number of types of electrodes can be suitable in the practice of the invention, but it has been found that wire copper electrodes are particularly suitable. The area to which an electrode is to be applied is cleansed and cleared of any hair, wax, etc. Standard electrode jelly is used at the points of contact of the electrode. Preferably, the surface area of the electrodes that are in contact with the skin are relatively small in order to render the application of the signal more precise.

The lung, liver, and Shen Men acupoints have been found to be particularly suitable for the specific application of the electrode. The acupoints can be located with the assistance of the auditory sensor of an Alphastim instrument or other conventional devices. The fifth and seventh cranial nerves have termini in the ears and impedance is relatively low because of the lack of thick bone in these locations. In a particularly preferred embodiment, the electrodes are applied to the Shen Men points on either side of the head.

After the treatment with the transcranial electrical nerve stimulation is completed, psychological therapy is recommended in order to restructure the patient's life to make the patient more psychologically resistant to a relapse.

EXAMPLE 1

A patient addicted to heroin is first standardized in accordance with the present invention by administering a dose of methadone under clinical supervision. The amount of the dose is that amount which is equavalent to the amount of heroin which the patient is accustomed to taking. After most of the effects of the dose have subsided but before withdrawal symptoms occur, the patient is administered a signal having a frequency of 100 Hz and a pulse width of 0.22 msec. in a direct current. The signal is applied in trains of 100 seconds, separated by off periods of 100 seconds. This first stage of treatment is continued for 5 days.

At the end of the fifth day, the signal is changed to one having a frequency of 10 Hz and a pulse width of 1.5 msec. in an alternating current. The signal is applied intermittently and in trains of irregular duration. The irregularity of the trains and the off periods that separate them is such that the first on and off periods are of a duration of one minute each, the second are of a duration of 10 minutes each, the third are of a duration of 100 minutes each, the fourth are of a duration of 1000 minutes each, the fifth are of a duration of 100 minutes each, the sixth are of a duration of 10 minutes each, and the seventh are of a duration of one minute each. This progression is repeated throughout the application of the low frequency signal for two days. At the end of the second day, the off periods are successively increased to 6 hours over a period of three days. The patient is provided psychological counseling at the end of the electrical treatment.

EXAMPLE 2

A patient suffering from an habituation to Nembutal is administered a dose of the drug of abuse under clinical supervision and before the withdrawal symptoms for the drug begin, the patient is administered a signal having a frequency of 25 to 35 Hz and a pulse width of 0.1 msec. in an alternating current. The signal is applied intermittently in trains having an average duration of 30 seconds, each separated by off periods having an average duration of 30 seconds. The specific duration of a particular train or off period is determined randomly, the range of durations for specific trains or off periods being 10 to 50 seconds. During a sleep period, the signal is changed to one having a frequency of 10 Hz and a pulse width of 1.5 msec. This signal is applied constantly during sleep periods after one day of treatment.

The entire treatment is applied for 5 days before a weaning off process is instituted. During the weaning off process, the duration of the off periods is progressively increased.

EXAMPLE 3

A patient addicted to Valium is standardized by administering a dose of the drug of abuse. Before withdrawal symptoms are manifest, a signal having a frequency of 200 Hz and a pulse width of 0.5 msec. is applied in a direct current. The signal is applied intermittently in trains of 200 seconds each, separated by off periods of 200 seconds. The treatment lasts for 10 days.

EXAMPLE 4

A patient addicted to cocaine is standardized by administrating a dose of cocaine in a clinical setting. Before withdrawal symptoms are experienced, a signal having a frequency of 30 Hz and a pulse width of 0.1 msec. is applied in an alternating current. The signal is applied intermittently, wherein the average period of application of the signal is 30 seconds and the average off period is 30 seconds. The actual durations of specific periods of application and off periods range between 15 and 45 seconds and the treatment is administered for 7 days.

EXAMPLE 5

A patient addicted to Dexedrine is standardized by administering a dose of Dexedrine at the onset of treatment. Before withdrawal symptoms occur, a signal having a frequency of 200 Hz and a pulse width of 0.5 msec. is applied in a direct current. The signal is applied intermittently in trains having a duration of 200 seconds, each train separated from another by an off period of 200 seconds. During sleep, the pulse width of the signal is increased to 1.5 msec. and the treatment lasts for 6 days.

EXAMPLE 6

Before a cigarette-smoker experiences a craving for a cigarette, a signal having a frequency of 5 Hz and a pulse width of 0.1 msec. is applied in an alternating current. The signal is applied intermittently in equal on and off cycles. Initially, the duration of the on and off cycles are each 5 seconds, but this duration increases in a fixed arithmetic progression by increments of one minute to a maximum duration of just over 30 minutes each, at which point the duration of the on and off periods decreases progressively in one minute increments, finally returning to the original 5 second periods. The progression is repeated four additional times over a period of 7 days.

EXAMPLE 7

A patient addicted to alcohol is administered an appropriate dose of alcohol at the initiation of the treatment. Before withdrawal symptoms are evidenced, a signal having a frequency of 10 Hz and a pulse width of 0.1 msec. is applied in an alternating current. The signal is applied intermittently, wherein each of the on and off periods has an average duration of 10 seconds, the actual durations of specific periods being selected at random in the range between 2 and 25 seconds. During a sleep period, the frequency is increased to 30 Hz, the pulse width is increased to 1.5 msec., and the signal is applied continuously. The treatment lasts for 12 days.

EXAMPLE 8

In the treatment of an addiction to cannabis, a patient is standardized by being administered an appropriate dose of cannabis at the outset of the treatment. Before withdrawal symptoms are experienced, a signal having a frequency of 200 Hz and a pulse width of 0.5 msec. is applied in a direct current. The signal is applied intermittently, wherein the on periods and the off periods each are 200 seconds in duration. The treatment lasts for 4 days.

EXAMPLE 9

A patient suffering from lower back pain is treated by administering a signal having a frequency of 200 Hz and a pulse width of 1.5 msec. in a direct current. The signal is applied in trains having durations of 5 minutes, the trains being separated, successively, by off periods of 0.5, 1, 2 and then 4 minutes.

In addition to drug addiction, a number of other afflictions are treated in accordance with the present invention. These afflictions include stress, insomnia, appetite disturbances, and pain. Treatments for stress and insomnia are related, since an objective of such treatments is, at least in part, to relax the patient. These conditions can be treated by extrapolation from the teachings set forth above. Appetite disturbances are also related to stress, and also with depression, and treatment of such disturbances can also be administered in accordance with the teachings set forth above. Further, because obesity is related to an overproduction of $\beta$-endorphin and anorexia is related to an inadequate production of $\beta$-endorphin, manipulation of the body's production of this substance by the application of appropriate electrical signals can overcome or ameliorate these conditions. The application of a signal having a frequency of 100 Hz and a pulse width of 0.22 msec. in a direct current will decrease $\beta$-endorphin production and a signal having a frequency of 10 Hz and a pulse width of 1.5 msec. in an alternating current will increase such production.

In addition to human subjects, the present invention is effective on laboratory animals such as rats, such that the efficacy of the invention can be demonstrated in a laboratory environment.

It will be apparent to those skilled in the art that many modifications and variations may be introduced without departing from the inventive scope of the present teachings.

I claim:
1. A method of treating a subject with an electrical signal transcranially comprising
   a first step of generating a first signal train comprising a plurality of pulses and applying said train across a subject's head,
   a second step of terminating the applying of said first signal train,
   a third step of applying no signal across said subject's head for a duration of a first off period,
   a fourth step of generating a successive signal train comprising a plurality of pulses and applying said trains across said subject's head,
   a fifth step of terminating the applying of said successive signal train,
   a sixth step of varying the duration of the applying of said successive train in respect to a duration of the applying of a preceding train,
   a seventh step of applying no signal across said subject's head for a duration of a successive off period,
   an eighth step of varying the duration of said successive off period in respect to a duration of a preceding off period, and a ninth step of repeating said fourth, fifth, sixth, seventh, and eighth steps such that an activation of nerves of said brain by said signal, comprising a series of trains and off periods the durations of which are varied in accordance with said sixth and eighth steps, is at a substantially continuous rate as the application of said trains and off periods proceeds.

2. The method of claim 1, wherein said signal has a frequency of at least about 100 Hz.

3. The method of claim 2, further comprising the step of substituting said signal with a signal having a frequency of at most about 35 Hz. when said subject experiences an adverse reaction to said method.

4. The method of claim 1, wherein said signal has a frequency of at most about 35 Hz.

5. The method of claim 4, further comprising the step of substituting said signal with a signal having a frequency of at least about 100 Hz. when said subject experiences an adverse reaction to said method.

6. The method of claim 1, further comprising the step of inhibiting the production of neurotransmitter in the brain.

7. The method of claim 1, further comprising the step of stimulating the production of neurotransmitter in the brain.

8. The method claim 1, wherein said signal has a frequency of about 100 Hz. and said method is used in the treatment of an addiction to drugs that are received by opiate receptors.

9. The method of claim 1, wherein said signal has a pulse width of about 0.22 milliseconds and said method is used in the treatment of an addiction to drugs that are received by opiate receptors.

10. The method of claim 1, wherein said signal has a frequency of about 10 Hz. and said method is used in the treatment of an addiction to drugs that are received by opiate receptors.

11. The method of claim 1, wherein said signal has a pulse width of about 1.5 milliseconds and said method is used in the treatment of an addiction to drugs that are received by opiate receptors.

12. The method of claim 1, wherein said signal has a frequency of about 25 to 35 Hz. and said method is used in the treatment of an habituation to barbiturates or barbiturate-like sedatives.

13. The method of claim 2, wherein said signal has a pulse width of about 0.1 milliseconds and said method is used in the treatment of an habituation to barbiturates or barbiturate-like sedatives.

14. The method of claim 1, wherein said signal has a frequency of about 10 Hz. and a pulse width of about 1.5 milliseconds and is used to encourage sleep in a treatment for an habituation to barbiturates or barbiturate-like sedatives.

15. The method of claim 1, wherein said signal has a frequency of about 200 Hz. and said method is used in the treatment of an addiction to benzodiazeapines.

16. The method of claim 1, wherein said signal has a pulse width of about 0.5 milliseconds and said method is used in the treatment of an addiction to benzodiazeapines.

17. The method of claim 1, wherein said signal has a frequency of about 30 Hz. and said method is used in the treatment of an addiction to cocaine.

18. The method of claim 1, wherein said signal has a pulse width of about 0.1 milliseconds and said method is used in the treatment of an addiction to cocaine.

19. The method of claim 1, wherein said signal has a frequency of about 200 Hz. and said method is used in the treatment of an addiction to amphetamines.

20. The method of claim 1, wherein said signal has a pulse width of about 0.5 milliseconds and said method is used in the treatment of an addiction to amphetamines.

21. The method of claim 1, wherein said signal has a frequency of about 200 Hz. and a pulse width of about 1.5 milliseconds and is used to encourage sleep in a treatment for an addiction to amphetamines.

22. The method of claim 1, wherein said signal has a frequency of about 5 to about 10 Hz. and said method is used in the treatment of an habituation to nicotine.

23. The method of claim 1, wherein said signal has a pulse width of about 0.1 or 0.22 milliseconds and said method is used in the treatment of an habituation to nicotine.

24. The method of claim 1, wherein said signal has a frequency of about 10 Hz. and said method is used in the treatment of an addiction to alcohol.

25. The method of claim 1, wherein said signal has a pulse width of about 0.1 milliseconds and said method is used in the treatment of an addiction to alcohol.

26. The method of claim 1, wherein said signal has a frequency of about 30 Hz. and a pulse width of about 1.5 milliseconds and is used to encourage sleep in a treatment for an addiction to alcohol.

27. The method of claim 1, wherein said signal has a frequency of about 200 Hz. and said method is used in the treatment of an habituation to hallucinogenic drugs.

28. The method of claim 1, wherein said signal has a pulse width of about 0.5 milliseconds and said method is used in the treatment of an habituation to hallucinogenic drugs.

29. The method of claim 1, wherein said signal has a frequency of about 200 Hz. and said method is used in the treatment of pain.

30. The method of claim 1, wherein said signal has a pulse width of about 1.5 milliseconds and said method is used in the treatment of pain.

31. The method of claim 1, wherein said signal has a frequency of about 10 Hz. and said method is used in the treatment of pain.

32. The method of claim 1, wherein said signal has a pulse width of about 0.22 milliseconds and said method is used in the treatment of pain.

33. The method of claim 1, further comprising the step of standardizing said subject prior to said applying step, said standardization step comprising the steps of clinically administering a dosage of a drug to which said subject is addicted or habituated, or a drug that is functionally equivalent to said drug to which said subject is addicted or habituated, to said subject and applying said signal after effects of said drug or said functionally equivalent drug have subsided and before said subject experiences withdrawal symptoms.

34. The method of claim 1, wherein said signal has a rectangular wave form.

35. The method of claim 1, further comprising the step of generating said signal in a rectangular wave form comprising a spike that occurs at the onset of positive segments of the pulses of said signal.

36. The method of claim 1, wherein the voltage of said applied signal is about 1 volt.

37. The method of claim 1, further comprising the step of monitoring characteristics of said signal on an oscilloscope.

38. The method of claim 1, further comprising the step of determining the duration of said trains and said off periods by an arithmetic progression.

39. The method of claim 1, wherein the pulses applied across said subject's head have an equal amount of positive and negative segments such that there is a zero net voltage applied across said subject's head.

40. The method of claim 1, wherein the duration of off periods between pulse trains in between 5 and 10 seconds.

* * * * *